(12) United States Patent
Merce Vives

(10) Patent No.: US 6,630,107 B1
(45) Date of Patent: Oct. 7, 2003

(54) BLOOD PUMPING EQUIPMENT FOR EXTRACORPOREAL CIRCULATION AND VENTRICULAR ASSISTANCE

(76) Inventor: Salvador Merce Vives, Plaza América, 5-46004, Valencia (ES)

( * ) Notice: Subject to any disclaimer, the term of this patent is extended or adjusted under 35 U.S.C. 154(b) by 0 days.

(21) Appl. No.: 09/428,906

(22) Filed: Oct. 28, 1999

(30) Foreign Application Priority Data

Oct. 28, 1998 (ES) ............................................. 9802264

(51) Int. Cl.⁷ .......................... A61M 1/36; A61M 37/00
(52) U.S. Cl. ...................... 422/45; 604/6.11; 604/6.13; 604/6.14
(58) Field of Search ................... 422/44–48; 604/4.01, 604/6.11, 6.13, 6.14

(56) References Cited

U.S. PATENT DOCUMENTS

| | | | | |
|---|---|---|---|---|
| 3,898,045 A | * | 8/1975 | Bowley | 128/DIG. 3 |
| 4,490,331 A | | 12/1984 | Steg, Jr. | 422/46 |
| 5,043,140 A | * | 8/1991 | Combs | 128/DIG. 3 |
| 5,270,005 A | * | 12/1993 | Raible | 128/DIG. 3 |
| 5,411,706 A | * | 5/1995 | Hubbard et al. | 210/321.75 |
| 5,770,149 A | | 6/1998 | Raible | 422/46 |
| 5,823,986 A | * | 10/1998 | Peterson | 422/44 |
| 5,879,624 A | * | 3/1999 | Boehringer et al. | 210/645 |
| 5,916,191 A | * | 6/1999 | Plunkett et al. | 604/6.11 |

FOREIGN PATENT DOCUMENTS

| | | |
|---|---|---|
| ES | 2011147 | 12/1989 |
| WO | 9204060 | 3/1992 |

* cited by examiner

*Primary Examiner*—Angela D. Sykes
*Assistant Examiner*—Leslie R Deak
(74) *Attorney, Agent, or Firm*—Klauber & Jackson

(57) ABSTRACT

The equipment comprises an impulsion pump (5-5') with a displaceable piston (7), that adopts a bellows shape, located in the inside of the same, the chamber of the pump receiving the patient's venous blood from a reservoir (4). In the communication (16) between the reservoir and the chamber a float valve (17) has been provided for, a valve that closes the passage when the piston (7) impels the blood through a nozzle (15), passing through a valve (22), then through a heat exchanger (28) and then through an oxygenator (29) from which the oxygenated blood is sent once again to the patient. The shaft (9) of the nozzle (7) is operated by a mechanism (14) that transforms the rotating and alternate movements of a servomotor (12) into linear movements, the operation of this servomotor (12) being controllable by means of a computerized console, permitting a pulsatile blood flow to be provided with adjustable flow and frequency. The equipment forms a disposable fungible unit, used to substitute the pumping action of the heart of a patient, when he is subjected to heart surgery or ventricular assistance.

13 Claims, 3 Drawing Sheets

BLOOD PUMPING EQUIPMENT FOR EXTRACORPOREAL CIRCULATION AND VENTRICULAR ASSISTANCE

As expressed in the title of this specification, the present invention, refers to blood pumping equipment for extracorporeal circulation, whose purpose is to substitute the pumping action of the heart of a patient when the patient is subjected to heart surgery, it likewise being useful as a support means of ventricular assistance, respiratory assistance and cerebral percussion, without ruling outs its use in dialysis.

The purpose of the invention is to integrate in a single fungible unit the elements or means that are used in pumping blood for extracorporeal circulation, permitting the replacement of this unit or assembly after each operation, with a minimum loss of time, easy assembly/disassembly and with an economic cost much lower than that implied by systems or equipment used conventionally for the same purposes, eliminating the length of tubes and the volume of blood that would be involved. Basically, the equipment comprises a reservoir receiving the patient's venous blood; an impulsion pump of that blood; a heat exchanger for thermal conditioning of the blood and an oxygenator, all complemented with corresponding valves in order to form a single assembly or unit that permits a pulsatile blood flow to be provided with adjustable flow and frequency, by the doctor himself or controlled by a signal of the patient's electrocardiogram.

BACKGROUND OF THE INVENTION

As is well known, heart surgery in extracorporeal circulation operates on a stopped heart, therefore it is necessary to temporarily substitute the functioning thereof by means of a system that externally pumps the blood, thus maintaining the blood perfusion to the brain and to the rest of the vital organs of the body.

Nowadays the main types of systems used in the pumping of blood are based on peristaltic or centrifugal pumps. Both systems provide a flow fixed by unit of time, therefore in order to increase the flow its speed must be increased, which leads to the continuous blood diverging very considerably from the natural pulsatile flow generated by the human heart.

Taking into account that the greater the disparity between the natural blood flow and the flow generated by the pumping system, the greater the physiological deterioration suffered by the patient, it is evident that it proves to be logical and desirable to achieve the greatest approximation between the extracorporeally pumped blood flow and the natural pulsatile flow.

Systems or equipment that efficiently carry out this function are unknown, irrespective of the fact that current systems are constituted by several parts that need to be coupled together before the operation, having high losses of charge, and the subsequent loss of time in the preparation, and, what is even more important, without the desired optimum results.

Besides, it must be taken into account that the equipment used is disposed of after each operation, which implies a high cost.

DESCRIPTION OF THE INVENTION

The equipment object of the invention, provided for the pumping of blood for extracorporeal circulation and ventricular assistance, constitutes a unit or assembly integrated with an operating principle that permits the programming of pumping flows and frequency in an independent manner, with the particularity that the impulsion pump may be controlled by a computer (according to the doctor's orders or as of a measured physiological parameter), which permits the obtainment of flow and pressure waves with characteristics close to those existing in normal physiological operation.

Therefore, it may be said that the equipment of the invention implies a structurally simple solution with absolute functional reliability, for the purpose for which it has been developed, maintaining its fungible characteristics.

In this sense, the equipment in question is constituted as of a pump with a bellows-type piston, which comprises a chamber in which the piston itself is arranged, piston integral to a through shaft, in a sealed manner, through a cover that closes the bottom base of the chamber, whose shaft is operated by means of a servomotor related to a suitable mechanism that transforms the angular alternate movement at the outlet of the servomotor into linear alternate movement that is applied to the shaft of the piston, so that the piston is displaced alternately in an axial manner in the inside of the chamber, in order to achieve in one direction of displacement the input of the patient's venous blood to the chamber, and to produce in the other direction of displacement the impulsion of the blood to the outside from said chamber for the oxygenation thereof.

In relation to the cited chamber established in the impulsion pump, the same is communicated on the one hand with a reservoir or tank to which the patient's venous blood accedes, reservoir that is placed above the chamber and integral to the body thereof. In the inside of the chamber, specifically in the area of passage or communication thereof with the reservoir, there is a float sealing valve, which due to its low density with regard to that of the blood is pushed by the blood towards the closing position, when the blood contained in the chamber is impelled by the piston (by means of expansion of the bellows) towards the outlet nozzle, while when the piston is displaced in the opposite direction (the bellows contracts), increasing the capacity of the chamber, the valve is separated from the passage of communication with the reservoir, opening said passage and permitting the access of the venous blood from the cited reservoir to the chamber itself.

Therefore, the chamber from which the pumping of the blood takes place is variable in amplitude, which permits the variation of the flow maintaining the frequency and vice versa, therefore said two parameters may be controlled independently in order to adapt them to the patient's or doctor's needs.

The body of the cited chamber is assembled, with ease of becoming independent, on a base with suitable displacement means, such as wheels, that allow easy transfer of the equipment from one place to another; locking and securing means of said assembly having been provided for between said two parts, with the particularity that the bottom one constituting the cited base carries the mechanism that transform the rotating movement of the servomotor into alternate linear movement on the shaft of the piston, the servomotor also being assembled on said base.

On the other hand, a ball-check valve that closes the passage by gravity has been provided for on the duct corresponding to the outlet nozzle of the chamber in which the impulsion pump is established, in such a way that the opening is carried out only when the blood is impelled from the pump. After said ball-check valve a heat exchanging device is inserted, as a thermal conditioning means of the blood and, connected to the latter, a oxygenating device, from which the oxygenated blood comes out through a nozzle, returning to the patient. Said thermal conditioning and oxygenating devices are integral to the block formed by the reservoir and body of the pump, in such a way that said components or elements, including the valves, form a fungible assembly or unit, easily assembled/disassembled with regard to the base.

The cited integration gives rise to a single fungible unit or assembly, and entails the elimination of the operative phases in order to carry out the coupling of all of the independent elements, intercommunicating them with tubes, which implies a saving of material, installation and final disassembly time, to which it is necessary to add the saving of volume of blood existing in the circuit outside of the patient, a fact which is of the utmost importance, aside from eliminating with this part of the effect of hemolysis that the cited tubes produce.

The incorporation of a programmable automaton or computerized console, that governs the servomotor in order to control the movement of the bellows-type piston and consequently the flow and frequency of the pump, is also characteristic of the invention, the programming being carried out by means of a PC on the market, that makes the calculations and establishes the communication with the automaton that controls the servomotor, there also being a screen for direct control of said automaton, it being possible to achieve that the performance of the equipment is similar to that of human physiological behavior, with some pressure and flow curve diagrams similar to those of the behavior of the blood system, evidencing the similarity achieved in the parameters achieved with elasticity in frequency, volume, pressure and curve form.

The fact that the equipment may be provided with an autonomous operation system should be pointed out, by means of an electric feed battery, that permits the patient to be transported while some organ of his is being assisted by the proposed equipment, it also being provided for that the computerized console and the equipment itself are connected to each other by means of a cable with an indefinite length, permitting the equipment to be located next to the patient or next to the surgeon, the console being able to be separated in a second plane.

Finally, the possibility of providing the equipment with means to adjust its operation tempo should be cited, means alternate to the console, for the purpose of permitting the use thereof without conventional electric feed.

BRIEF DESCRIPTION OF THE FIGURES

In order to complement the description that is going to be made hereinafter and for the purpose of helping to provide a better understanding of the characteristics of the invention, the present specification is accompanied by a set of drawings on the basis of which the innovations and advantages of the blood pumping equipment for extracorporeal circulation made in accordance with the object of the invention, will be more easily understood.

DESCRIPTION OF THE PREFERRED EMBODIMENT

Figure 1:
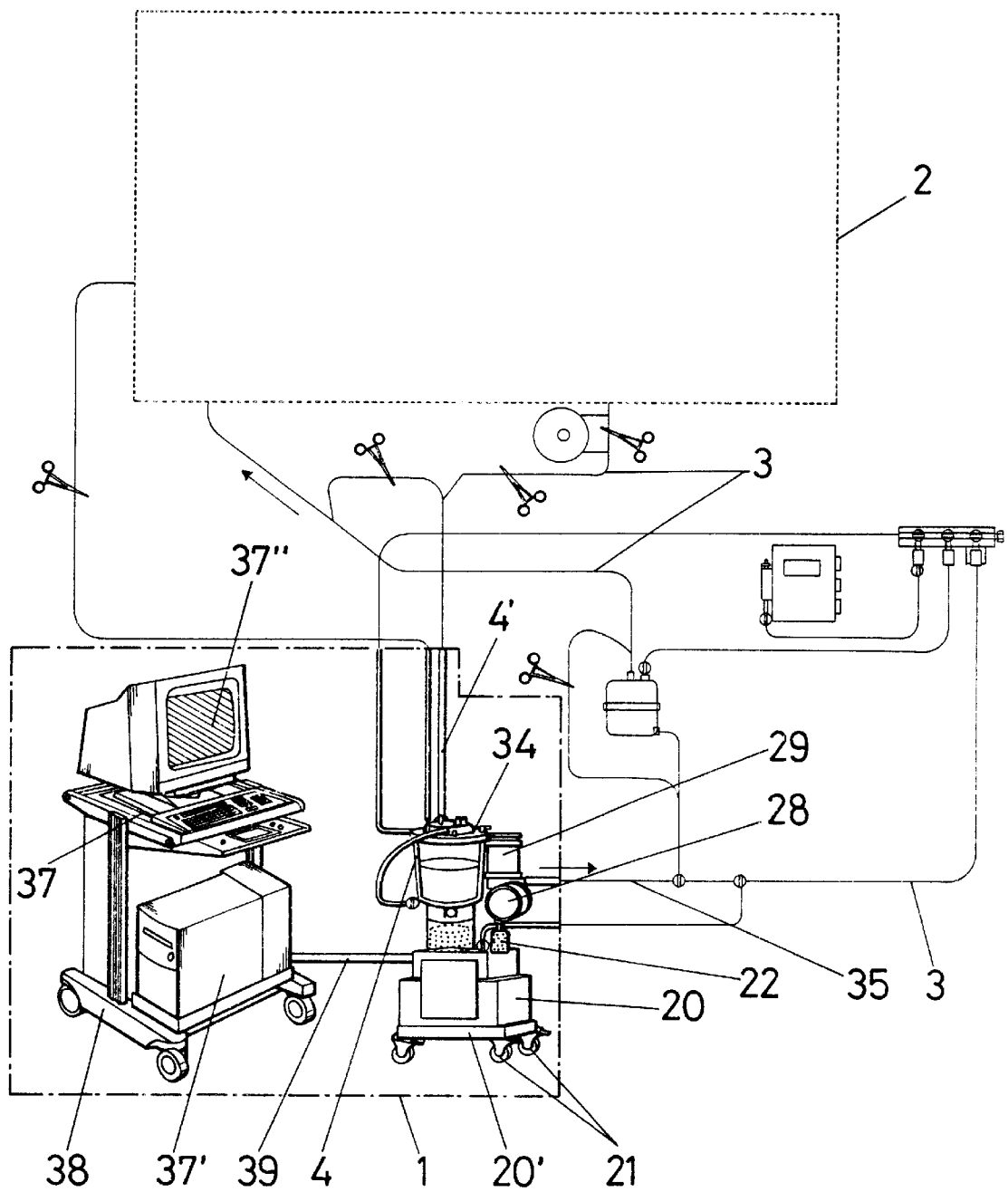
FIG. 1 is a schematic representation according to a general perspective of the equipment of the invention, as well as a block that corresponds to a simulator of the patient conveniently connected to the equipment.

As can be seen in the cited figures, and specifically in connection with FIG. 1, it can be seen how the equipment of the invention, delimited by the contour generally referred to as number (1), is provided for its connection to a patient, whose simulator corresponds to the contour delimited by reference (2), this connection being established by means of tubes (3) and other devices and conventional components that do not have to be referred to as they are not object of the invention.

In relation to the equipment of the invention, the same comprises a reservoir (4) in the manner of a tank, provided with an inlet (4') to receive the venous blood coming from the patient. This reservoir (4) is coupled at the top on a body (5) constituting an impulsion pump, whose body (5) is defined by two parts, one corresponding to reference (5) itself and the other one corresponding to reference (5'), connected together by threading or by any other conventional system with the insertion of a sealing gasket (6), with the particularity that part (5') is the one that constitutes the coupling means for the top reservoir (4). A piston (7) with the capacity of axial displacement is assembled in the inside of body (5), and whose piston includes a bellows (8) and is integral to a shaft (9) guided on a bushing (10) provided on a bottom closing cover. The body (5-5') defines a chamber whose capacity is adjustable, depending on the position of the piston (7), in other words, on the greater or lesser extensibility of the bellows (8) belonging to said piston (7), extensibility and/or contraction that is achieved by means of upward and downward axial displacement of the shaft itself (9), that is operated from a servomotor (12) in which its shaft (13) is coupled to a mechanism (14) by means of which the rotating alternate movement of the shaft (13) belonging to the motor (12) is transformed into linear alternate movement of the shaft (9) corresponding to the piston (7).

The body (5-5') defines inside a chamber and as a whole an impulsion pump of the blood from the reservoir (4) towards an outlet nozzle (15), in such a way that the base hole for communication (16) between the reservoir (4) and the body chamber (5) or impulsion pump itself, may open and close by means of a float valve constituted by a low density sphere (17), that moves upward and downward between some side guides (18) that are curved at their bottom part in order to define an opening smaller than the diameter of the sphere (17), so that the sphere is maintained duly guided and positioned so that when it rises it carries out the closing of the passage or opening (16), against the corresponding sealing gasket (19) provided for therein.

The mechanism (14) that connects the shaft (9) of the piston (7) and the servomotor (12) is assembled on a frame (20) with respect to which the body (5-5') with the reservoir (4) may become independent, and whose frame (20) is in turn fastened on a displaceable base (20') provided with bottom wheels (21).

Figure 3:
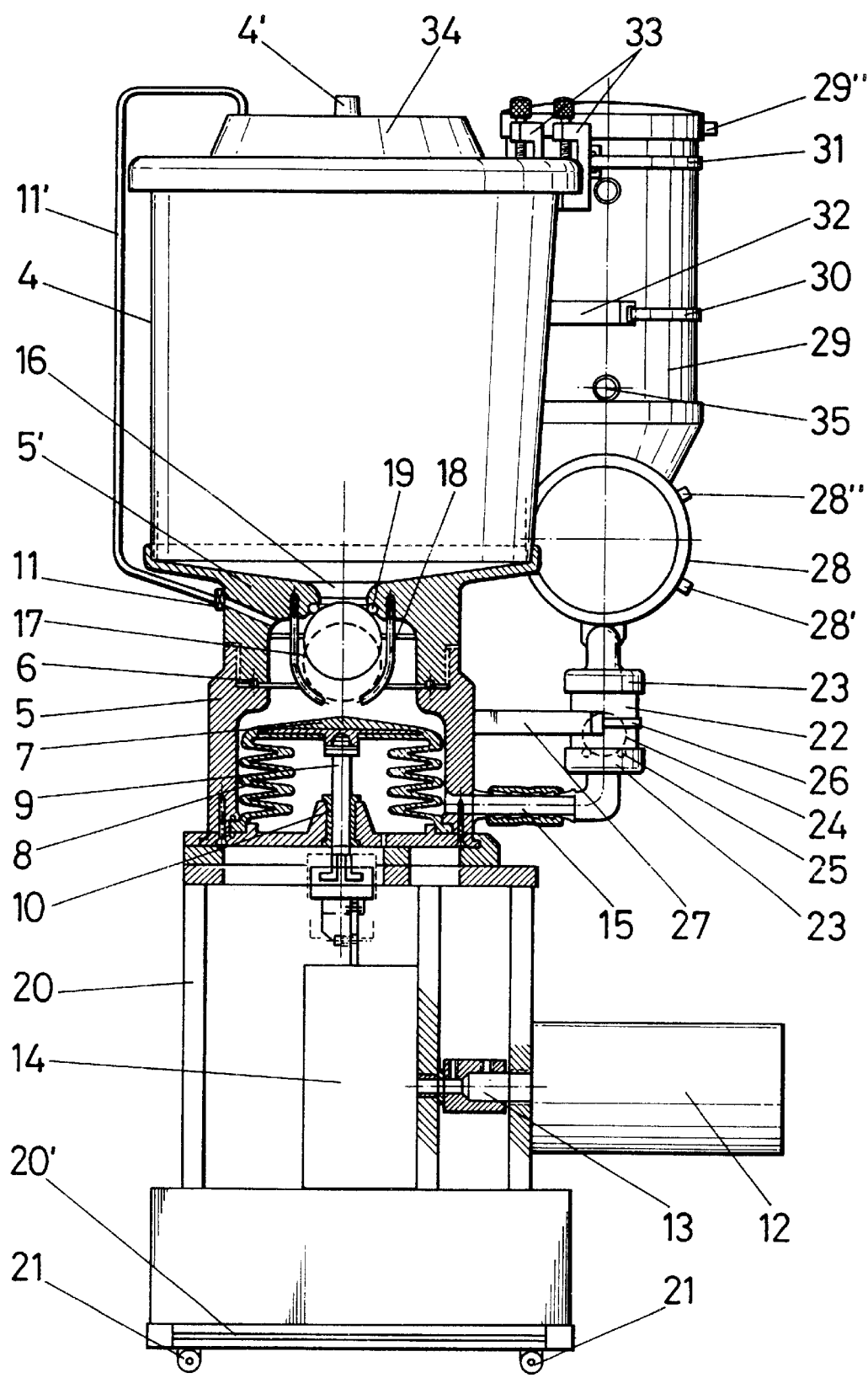
FIG. 3 is a raised view, with a sectioned part, of the same equipment represented in the preceding figure, allowing one to see the constitution of the impulsion pump, its coupling to the base and the means for transmitting force from the servomotor to the shaft of the bellows-type piston that forms part of the impulsion pump.

After the outlet nozzle (15) of the body (5-5') constituting the impulsion pump, a gravity ball-check valve has been provided for, a valve constituted as of a cylindrical hollow body (22) with respective top and bottom closing covers (23), and inside it there is a sphere (24) that tends, due to its weight, to close by gravity the inlet from the nozzle (15) to the inside of the body (22), carrying out the closing on the corresponding sealing gasket (25), as shown by the dash line in FIG. 3. This valve body (22) is integral, with a releasable nature, to the body (5) of the impulsion pump, by means of a brace (26) connected to a support (27) which in turn is integral to said body (5). After the ball-check valve (22) there is a heat exchanger (28), for thermal conditioning and then an oxygenator (29), these two elements forming a single body that is fastened to the reservoir (4) by means of braces (30) and (31), the brace (30) being fastened to a support (32) integral to the body itself of the reservoir (4), while the brace (31) is fastened to some clamps (33) that can be fastened on the top cover (34) of the reservoir itself (4). The oxygenator (29) is provided with the corresponding outlet (35) for the already oxygenated blood that will be returned to the patient himself.

Figure 2:
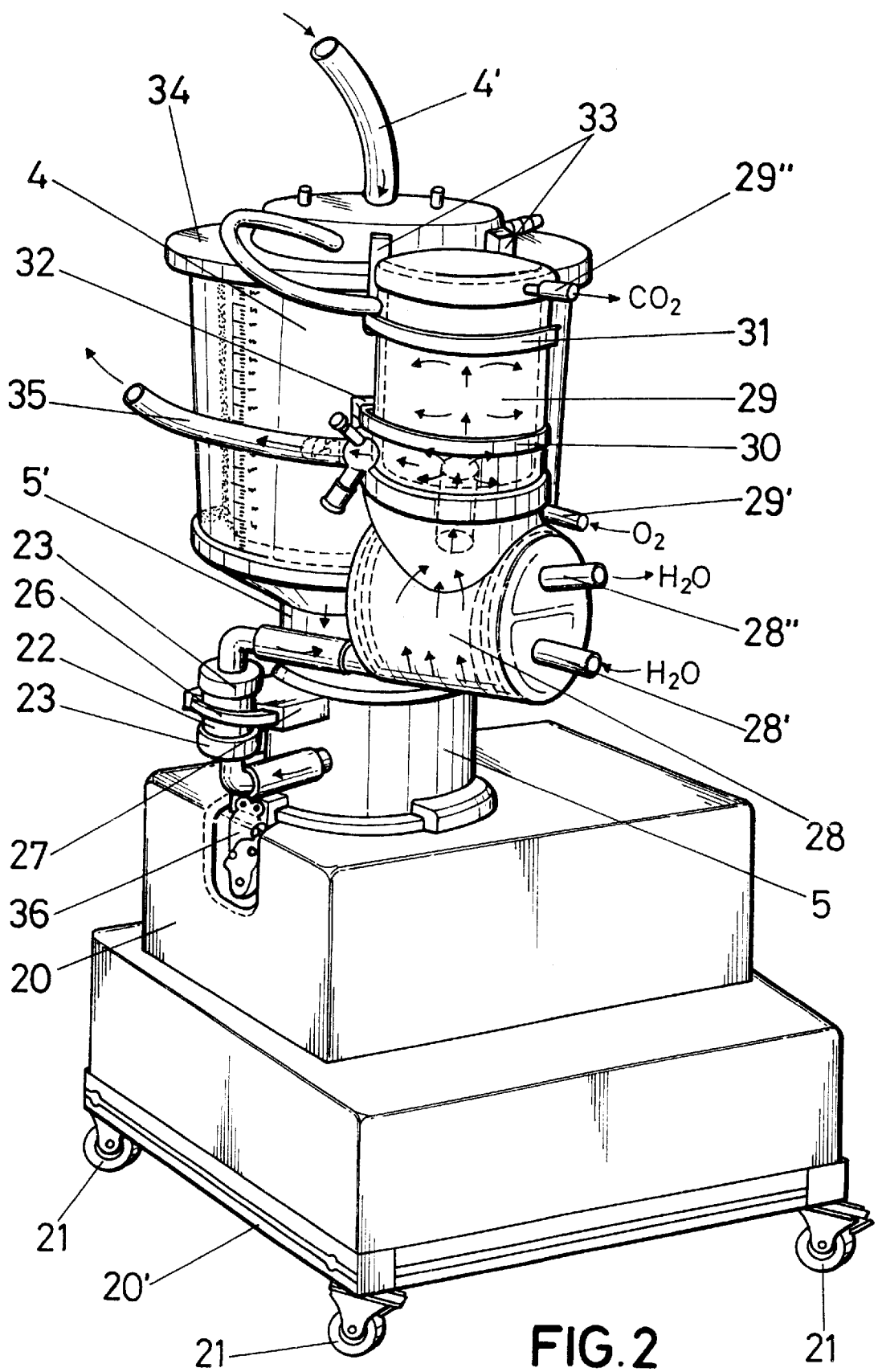
FIG. 2 shows a perspective view of the equipment object of the invention, wherein all of its parts can be seen.

In the assembly of the body (5) of the impulsion pump on the bottom frame (20) a safety fastening (36) has been provided for, as shown in FIG. 2, wherein the inlet (28') of hot water to the heat exchanger (28) and the outlet (28") of cold water from the exchanger (28).

Likewise, the oxygenator (29) includes an inlet (29') for oxygen and an outlet (29") for carbon dioxide. The assembly that the reservoir (4), impulsion pump or body (5-5'), heat exchanger (28) and oxygenator (29), form with their corresponding valves as commented, constitute a disposable fungible unit that may be easily and rapidly assembled with regard to the frame (20), permitting the indefinite use thereof with its corresponding displaceable base (20') to which the above cited disposable unit may logically be coupled and decoupled, unit that constitutes the blood pumping equipment for extracorporeal circulation and ventricular assistance.

The operation is as follows:

When the servomotor (12) starts operating, the shaft (13) thereof turns alternately producing alternate movements, previously transformed into linear ones, on the shaft (9), which gives rise to axial displacement of the shaft in the inside of the chamber of the body (5), or that is to say extensibility and/or contraction of the bellows (8), giving rise in the first case to an impulsion of the blood contained in the chamber of the body (5) through the nozzle (15), in whose operating phase the low density sphere (17) is pushed upward pressing against the gasket (19) and therefore closing the passage or hole (16) for communication with the reservoir (4). In the second case, in other words when the bellows (8), by axial displacement downward of the shaft (9), contracts, then the sphere (17) is separated from the gasket (19) permitting the passage of blood through the hole (16) from the reservoir (4) to the chamber of the impulsion pump or body itself (5), all of this according to the alternate rotating movements of the servomotor (12), which can evidently be controlled and regulated at the will of the medical staff. In the impulsion of the pump, in other words, in the impulsion of the blood from the chamber of the body (5) through the nozzle (15), the opening of the valve (22) will be produced by pushing the sphere (24) upward, which will close the passage when there is no blood impulsion, closing that will be carried out by gravity as it has already been said.

It is noteworthy that as the reservoir (4) and the impulsion pump are conveniently associated, the aspiration of blood is carried out in negative pressure, really low, which benefits the conditions of preservation and oxygenation of the blood, very effectively avoiding the phenomenon of cavitation.

As it has also been stated, the servomotor (12) may also be controlled as far as its speed is concerned and to its angular rotation, controlling with it the displacements of the piston (7) and the pumping frequency, which is carried out by means of a computerized console (37) that controls the different operating alternatives at the discretion of the doctor and/or the patient's measured physiological parameters, permitting the independent control of the pulse rate as well as of the blood flow. This computerized console (37) is programmable by means of a PC (37') associated to the corresponding screen or monitor (37") for direct control of the automaton or computerized console.

Likewise, the equipment has means to purge the air of the top area of the pumping chamber, which is very important in order to prevent serious inconveniences that this accumulation of gas can produce in the operation of the equipment and/or patient, carrying out the priming prior to connection to the patient.

The cited purging means, as shown in FIG. 3, are formed by a purging valve (11) and the respective duct (11") for return to the reservoir (4).

The assembly that has just been commented on is assembled on a rolling support (38), as shown in FIG. 1, and connected to the equipment of the invention by means of an interconnecting cable (39), with an indefinite length, for the purpose of permitting the use of the equipment at the desired distance with respect to the control console, permitting the console to be located anywhere and the equipment located next to the surgeon and/or patient.

Optionally, the equipment may be complemented with mechanical manually operated means that permit the same operation to be maintained in the event of a possible interruption in the feed of the electric fluid.

What is claimed is:

1. Blood pumping equipment for extracorporeal circulation and ventricular assistance having:
    a reservoir for receiving venous blood from a patient;
    a pump coupled under the reservoir, said pump including
        a body having
            an internal chamber wherein a pumping means for impelling blood is arranged,
            a first inlet providing a passage for communicating the reservoir with the internal chamber,
            a first outlet;
    a heat exchanger for thermal conditioning of blood;
    a nozzle for connecting the first outlet with the heat exchanger;
    an oxygenator arranged downstream of the heat exchanger;
    said blood pumping equipment comprising:
        a first valve provided for in the first inlet, said first valve having
            a closed position for preventing blood from passing from the internal chamber to the reservoir and
            an open position for allowing blood to pass from the reservoir to the internal chamber;
        a second valve provided between the nozzle and the heat exchanger;
    said blood pumping equipment being connected to a computerized console for controlling operating alternatives according to any of a doctor's criterion, a plurality of measured physiological parameters of a patient and combinations thereof, for permitting independent control of
        pulse rate and
        blood flow per pulse
    to generate a pulsating physiological flow by the pumping means acting in combination with the first valve;

the first valve being in the open position for enabling the pumping means to suck and the first valve being in the closed position for enabling the pumping means to impel.

2. The blood pumping equipment according to claim 1, wherein the body of the pump comprises two portions axially fastened having an internal chamber.

3. The blood pumping equipment according to claim 1, wherein the pumping means comprises a piston provided with bellows.

4. The blood pumping equipment according to claim 3, further comprising:

a servomotor having a first shaft;

a second shaft for integrally assembling the piston;

a mechanism between the first shaft and the second shaft for converting rotating alternate movements of the first shaft into linear alternate movements on the second shaft.

5. The blood pumping equipment according to claim 4, wherein the first valve comprises a low density first sphere for being closed against an O-ring seal provided for in the first inlet, the bellows being contracted and the first sphere being pushed towards an open position by weight of the blood in the reservoir for permitting blood to flow towards the internal chamber;

the bellows being expanded by upward displacement of the second shaft and the first sphere being pushed towards a closed position to impel the blood from the internal chamber towards the first outlet;

the first sphere being guided in displacement by guiding means for establishing a passage for blood.

6. The blood pumping equipment according to claim 1, wherein the reservoir, the body of the pump, the second valve, the heat exchanger and the oxygenator are preferably integrated in a single block.

7. The blood pumping equipment according to claim 1, wherein the second valve provided downstream from the nozzle comprises a tube-shaped body in vertical arrangement and a second sphere inside said tube-shaped body, the second valve:

being closed by gravity by said second sphere;

being open by means of an impelling force of the blood coming from the internal chamber.

8. The blood pumping equipment according to claim 7, wherein the tube-shaped body of the second valve is fastened to the body of the pump by means of a support integral to the body of the pump, and provided with a brace that is adapted on a side surface of the tube-shaped body of the second valve.

9. The blood pumping equipment according to claim 1, wherein the heat exchanger comprises a blood inlet, a hot water inlet, a cold water outlet;

the heat exchanger is integral to and communicated with the oxygenator;

the oxygenator includes an oxygen inlet, a carbon dioxide outlet, an oxygenated blood outlet;

the oxygenator is fastened in a removable manner to the reservoir by means of braces connected to a support and a plurality of clamps.

10. The blood pumping equipment according to claim 1, wherein said blood pumping equipment is a disposable fungible assembly that is assembled in a removable manner on a frame associated with a first displaceable base.

11. The blood pumping equipment according to claim 10, wherein the computerized console is connected to the disposable fungible assembly by means of an interconnecting cable of variable length for permitting to locate the computerized console at a distance form the disposable fungible assembly which is located next to a patient and/or surgeon.

12. The blood pumping equipment according to claim 11, wherein the computerized console comprises:

programming means for programming the computerized console;

calculating means for calculations being carried out in the computerized console;

communicating means for communicating the computerized console with a control automaton of the servomotor;

the computerized console, the programming means, the calculating means and the communicating means being arranged on a second displaceable support base.

13. The blood pumping equipment according to claim 1, further comprising purging means in a top portion of the internal chamber, said purging means comprising:

a purging valve located in a second outlet of the top portion of said internal chamber and a duct which is projected from said purging valve and is ended in a second inlet located in a top portion of the reservoir.

* * * * *